United States Patent
Krueger et al.

(12)

(10) Patent No.: US 6,193,892 B1
(45) Date of Patent: Feb. 27, 2001

(54) MAGNETIC SEPARATION ASSEMBLY AND METHOD

(75) Inventors: Julia E. Krueger; Steven T. Krueger, both of Deerfield; Cheryl M. Luedtke, Madison, all of WI (US)

(73) Assignee: Promega Corporation, Madison, WI (US)

( * ) Notice: Subject to any disclaimer, the term of this patent is extended or adjusted under 35 U.S.C. 154(b) by 0 days.

(21) Appl. No.: 09/261,356

(22) Filed: Mar. 3, 1999

(51) Int. Cl.$^7$ .................................................. B01D 35/06
(52) U.S. Cl. ...................... 210/695; 209/223.1; 209/636; 422/99; 422/101; 422/186.01; 435/288.4; 435/305.2; 435/809; 436/809; 210/222
(58) Field of Search ..................................... 210/222, 695; 422/99, 101, 186.01; 436/809; 209/223.1, 636; 435/288.4, 305.2, 809

(56) References Cited

U.S. PATENT DOCUMENTS

| | | |
|---|---|---|
| D. 221,220 | 7/1971 | Emmitt . |
| D. 280,130 | 8/1985 | Harkins et al. . |
| 2,510,591 | 6/1950 | Listman . |
| 2,540,364 | 2/1951 | Adams . |
| 3,954,016 | 5/1976 | Sarosy et al. . |
| 3,970,518 | 7/1976 | Giaever . |

(List continued on next page.)

FOREIGN PATENT DOCUMENTS

| | | |
|---|---|---|
| 0136126 A2 | 4/1985 | (EP) . |
| 0209490 A2 | 1/1987 | (EP) . |
| 0209490 A3 | 1/1987 | (EP) . |
| 0605003 A2 | 7/1994 | (EP) . |
| 0605003 A3 | 7/1994 | (EP) . |

OTHER PUBLICATIONS

"Molecular Biology/Reagent Systems", p. 151, Magne-Sphere® Technology Accessories—published sufficiently before filing date such that the date is not an issue.
Dynal® Brochure, 1994, Dynal® MPC®–6 and MPC®–P–12 Magnetic Particle Concentrators (4 pages)—published sufficiently before filing date such that month is not an issue.
http://www.corninglabware.com/ Corning Labware & Equipment, 1997 electronic catalog (1 page).

(List continued on next page.)

*Primary Examiner*—David A. Reifsnyder
(74) *Attorney, Agent, or Firm*—Michael Best & Friedrich LLP; Grady J. Frenchick; Paul F. Donovan (57) ABSTRACT

Provided are a magnetic particle separation assembly and method for separating a magnetically responsive complex from a non-magnetic test media in which the magnetically responsive complex is suspended. The assembly comprises an invertible rack for holding specimen containers and a magnetic support member for supporting the rack. The magnetic support member has a base and a planar member bisecting the base and extending upwardly therefrom. The planar vertical member has a plurality of magnets embedded therein. The magnets are disposed in a substantially horizontal orientation parallel to the base and spaced from the base. The invertible rack has a slot therethrough dimensioned to accept the planar vertical member of the magnetic support member. In one position, at least one container of a particular size is positioned within the rack so as to be adjacent to the magnetic support member in final assembly such that the magnetically responsive complex is separated from the non-magnetic media. In a second position in which the rack is inverted with respect to the support member, at least one other container of a different size is positioned within the rack in order to accomplish a similar separation result.

22 Claims, 5 Drawing Sheets

U.S. PATENT DOCUMENTS

| | | | |
|---|---|---|---|
| 3,985,649 | 10/1976 | Eddelman . | |
| 4,018,886 | 4/1977 | Giaever . | |
| 4,116,564 | 9/1978 | Renaud et al. . | |
| 4,124,122 | 11/1978 | Emmitt . | |
| 4,141,687 | 2/1979 | Forrest et al. . | |
| 4,157,581 | 6/1979 | Keiichi et al. . | |
| 4,168,460 | 9/1979 | Menke . | |
| 4,179,123 | 12/1979 | Tsukuda . | |
| 4,187,462 | 2/1980 | Haker et al. . | |
| 4,193,198 | 3/1980 | Bauer . | |
| 4,199,265 | 4/1980 | Sanderson et al. . | |
| 4,272,510 | 6/1981 | Smith et al. . | |
| 4,294,016 | 10/1981 | Wilkerson . | |
| 4,345,843 | 8/1982 | Berglund et al. . | |
| 4,375,407 | 3/1983 | Kronick . | |
| 4,411,868 | 10/1983 | Noack . | |
| 4,438,068 | 3/1984 | Forrest . | |
| 4,587,221 | 5/1986 | Cais et al. . | |
| 4,649,116 | 3/1987 | Daty et al. . | |
| 4,672,040 | 6/1987 | Josephson . | |
| 4,677,780 | 7/1987 | Shuman . | |
| 4,695,392 | 9/1987 | Whitehead et al. . | |
| 4,702,506 | 10/1987 | Iimura . | |
| 4,710,472 | 12/1987 | Saur et al. . | |
| 4,712,973 | 12/1987 | Garin et al. . | |
| 4,728,772 | 3/1988 | Smith . | |
| 4,738,773 | 4/1988 | Muller-Ruchholtz et al. . | |
| 4,751,053 | 6/1988 | Dodin et al. . | |
| 4,787,523 | 11/1988 | Kalous . | |
| 4,793,973 | 12/1988 | Ringrose . | |
| 4,813,294 | 3/1989 | Ukai et al. . | |
| 4,832,649 | 5/1989 | Konta . | |
| 4,895,650 | 1/1990 | Wang . | |
| 4,910,148 | 3/1990 | Sorensen et al. . | |
| 4,916,081 | 4/1990 | Kamada et al. . | |
| 4,922,226 | 5/1990 | Hsieh et al. . | |
| 4,935,147 | 6/1990 | Ullman et al. . | |
| 4,938,369 | 7/1990 | Carilli . | |
| 4,988,618 | 1/1991 | Li et al. . | |
| 4,999,459 | 3/1991 | Smith et al. . | |
| 5,014,141 | 5/1991 | Gervais et al. . | |
| 5,027,966 | 7/1991 | Yadock . | |
| 5,036,989 | 8/1991 | Carilli . | |
| 5,051,177 | 9/1991 | Dauchez . | |
| 5,098,663 | 3/1992 | Berthold et al. . | |
| 5,102,076 | 4/1992 | North et al. . | |
| 5,105,842 | 4/1992 | Wells . | |
| 5,108,933 | 4/1992 | Liberti et al. . | |
| 5,113,886 | 5/1992 | Wells et al. . | |
| 5,128,103 | 7/1992 | Wang et al. . | |
| 5,135,720 | 8/1992 | Uchida . | |
| 5,145,784 | 9/1992 | Cox et al. . | |
| 5,147,529 | 9/1992 | Lee et al. . | |
| 5,167,564 | 12/1992 | Lord . | |
| 5,169,603 | 12/1992 | Landsberger | 422/104 |
| 5,256,532 | 10/1993 | Melnicoff et al. | 435/5 |
| 5,264,042 | 11/1993 | Wells et al. | 134/21 |
| 5,279,936 | 1/1994 | Vorpahl | 435/6 |
| 5,318,914 | 6/1994 | Matte et al. | 436/526 |
| 5,336,760 | 8/1994 | Hardwick et al. | 530/413 |
| 5,340,749 | 8/1994 | Fujiwara et al. | 436/526 |
| 5,348,876 | 9/1994 | Michaelsen et al. | 435/240.2 |
| 5,349,296 | 9/1994 | Cikotte et al. | 324/309 |
| 5,368,203 | 11/1994 | Friedrich et al. | 222/179.5 |
| 5,385,280 | 1/1995 | Littlepage et al. | 224/42.45 |
| 5,385,822 | 1/1995 | Melnicoff et al. | 435/5 |
| 5,395,498 | 3/1995 | Gombinsky et al. | 204/182.8 |
| 5,411,863 | 5/1995 | Miltenyi | 436/6 |
| 5,429,927 | 7/1995 | Afseth et al. | 435/7.2 |
| 5,458,785 | 10/1995 | Howe et al. . | |
| 5,498,550 | 3/1996 | Fujiwara et al. | 436/526 |
| 5,506,130 | 4/1996 | Peterson et al. | 435/240.1 |
| 5,508,164 | 4/1996 | Kausch et al. | 435/6 |
| 5,512,439 | 4/1996 | Hornes et al. | 435/6 |
| 5,523,231 | 6/1996 | Reeve | 435/270 |
| 5,525,493 | 6/1996 | Hornes et al. | 435/91.2 |
| 5,536,475 | 7/1996 | Moubayed et al. | 422/101 |
| 5,541,072 | 7/1996 | Wang et al. | 435/7.21 |
| 5,567,326 | 10/1996 | Ekenberg et al. | 210/695 |
| 5,571,481 | 11/1996 | Powell et al. | 422/104 |
| 5,602,042 | 2/1997 | Farber | 436/526 |
| 5,639,669 | 6/1997 | Ledley | 436/177 |
| 5,641,622 | 6/1997 | Lake et al. | 435/2 |
| 5,646,004 | 7/1997 | Van Vlasselaer | 435/7.25 |
| 5,646,263 | 7/1997 | Ekenberg et al. | 536/25.4 |
| 5,648,223 | 7/1997 | Van Vlasselaer | 435/7.23 |
| 5,655,665 | 8/1997 | Allen et al. | 209/223.1 |
| 5,663,051 | 9/1997 | Vlasselaer | 435/7.23 |
| 5,665,582 | 9/1997 | Kausch et al. | 435/181 |
| 5,681,946 | 10/1997 | Reeve | 536/25.4 |
| 5,691,208 | 11/1997 | Miltenyi et al. | 436/526 |
| 5,693,784 | 12/1997 | Ekenberg | 536/25.4 |
| 5,695,989 | 12/1997 | Kalamasz | 435/308.1 |
| 5,698,271 | 12/1997 | Liberti et al. | 427/550 |
| 5,705,059 | 1/1998 | Miltenyi | 210/195.1 |
| 5,708,629 | 1/1998 | Hung-Hsu . | |
| 5,711,871 | 1/1998 | Miltenyi . | |
| 5,720,377 | 2/1998 | Lapeus et al. . | |
| 5,779,907 | 7/1998 | Yu . | |
| 5,897,783 | 4/1999 | Howe et al. . | |

OTHER PUBLICATIONS http://www.biometra.de/kit15.htm Kits for Molecular Biology, Sep. 18, 1997, Magnetic Separator Stand (1 page).

http://biochem.boehringer.com/ Boehringer Mannheim Research Biochemicals, 1996 (3 pages).

http://www.cpg–biotech.com CPG Inc. Online, Magnetic Particle Separators, Protocols Available, 1997 (3 pages).

http://www.cpg–biotech.com CPG Inc. Online, Magnetic Particle Separators, Instruction Manual for Product No. MPS0301, 1997 (2 pages).

http://www.cpg–biotech.com CPG Inc. Online, Magnetic Particle Separators, Instruction Manual for Product No. MPS0001, 1997 (2 pages).

Fig. 8

MAGNETIC SEPARATION ASSEMBLY AND METHOD

FIELD OF THE INVENTION

This invention relates, generally, to magnetic separation apparatus and methods in which magnetically responsive particles are used for isolating substances of interest from non-magnetic test media.

Particularly, the invention relates to a magnetic separation assembly having a magnetic support member and a removable invertible rack which can accommodate a variety of specimen container sizes. Moreover, the invention allows the user to efficiently manipulate multiple samples at any given time.

BACKGROUND OF THE INVENTION

Patient health care and biological research have made dramatic improvements in recent years, in part due to the utilization of assay techniques. Such assay techniques generally involve reacting a specimen to be assayed, usually a biological solution, e.g., blood, urine, tissue, cell, DNA, RNA, etc., with a magnetically responsive material, e.g., a magnetic containing material or a paramagnetic containing material, in a non-magnetic test media in a specimen container to produce a magnetically responsive complex. A magnetic field is applied or induced in or around the specimen container in order to isolate the magnetically responsive complex from the non-magnetic test media. Thereafter, either the magnetically responsive complex or the non-magnetic test media is withdrawn from the specimen container so that the magnetically responsive complex may be freed from the specimen material. The use of magnetic separation using solution and magnetic particles or complexes is well known in the art of diagnostic assay such as, but not limited to, immunoassay, genetic probe assay, ligand-receptor assay, protein-ligand assay, and hybridization-type assay. Apparatus and methods used to accomplish these types of assays vary from process to process and are well known in the art. The apparatus and methods can be of a non-automated type using a stationary magnet as disclosed in U.S. Pat. Nos. 3,985,649; 4,672,040; 4,695,392; 4,793,973; 4,935,147; 5,145,784; 5,279,936; 5,691,208; or of an automated or of a flow through type as disclosed in U.S. Pat. Nos. 3,970,518; 4,141,687; 4,375,407; 4,738,773; 4,910,148; 5,147,529; 5,318,914; 5,411,863; 5,536,475; 5,541,072; 5,602,042; 5,705,059; 5,711,871; 5,779,907; or of a type using a pin or magnetized means to dip into a container as disclosed in U.S. Pat. Nos. 4,272,510; 4,649,116; 4,751,053; 5,567,326; or of the stationary test tube rack magnetic separation type device with a magnetic member external to the container as disclosed in U.S. Pat. Nos. 5,571,481; 5,108,933; 4,988,618; 4,895,650; 4,438, 068; Des. 280,130. The aforementioned U.S. patent disclosures are incorporated herein by reference so as to illustrate the background of the invention and are not, by their inclusion, necessarily conceded to be prior art. The assembly according to the present invention relates to a stationary test tube rack magnetic separation type device with a magnetic member external to specimen containers.

Known stationary test tube rack magnetic separation devices are generally inconveniently sized to accommodate only one size of specimen container (e.g., a vial or a test tube or any single volume container), thereby requiring the extra expense of purchasing additional devices to accommodate different sizes of specimen containers.

Another problem with prior stationary test tube rack magnetic separation type devices concerns decanting the non-magnetic test media from the specimen containers. Many of the prior devices have rows of specimen containers oriented in multi-column, multi-row arrays, thereby preventing removal of the non-magnetic test media by simply decanting the media. The proximity of the rows and columns provides opportunities for cross contamination of the material found within the specimen containers if a simple decanting operation is performed by tipping the devices.

Yet another problem exists in prior devices where the stationary test tube rack magnetic separation devices have a longitudinally slidable magnetic member which slides into and out of a longitudinal bore which is closed at one end (see e.g., U.S. Pat. No. 5,571,481). Should there be any dirt or debris within the bore, the longitudinal member may bind and the magnets in the magnetic member may not properly align with the test tube sidewalls, thereby reducing the accuracy of the assay. In addition, there may be longitudinal slippage or sliding of the device as the longitudinally slidable member is aligned with and longitudinally inserted into the longitudinal bore. The slippage may cause interference with the test tubes or the solutions therein.

Still other problems exist in prior devices where the magnets of the stationary test tube rack magnetic separation devices are snap-fitted into place. The action of snapping one or more magnets to the appropriate mechanism may lead to spillage of the samples thereby causing less than accurate results or undesirable contamination. Additionally, when installing one or more magnets in the separation device, it is possible to position the magnet(s) in the wrong orientation which may lead to a poor separation result. Moreover, considering the strength of the magnets typically used in these prior devices, a free or removable magnet may create a hazardous situation. Such magnets, when not properly handled or stored, may tend to attach themselves to undesired hosts thereby possibly causing a multitude of problems as can be appreciated by those skilled in the art.

Another problem with prior stationary test tube rack magnetic separation type devices is the lack of efficient handling of multiple samples during both the mixing and separating operations.

SUMMARY OF THE INVENTION

What is needed is a magnetic particle or complex separation assembly having a removable invertible rack which can accommodate a variety of specimen containers, which permits decanting of the contents of the specimen containers without cross contamination of the contents of the specimen containers, which utilizes a magnetic support member adapted to conveniently receive the removable invertible specimen rack, and which is safe, easy and inexpensive to use, as well as easy to clean.

The present invention relates broadly to magnetic separation apparatus and methods in which magnetically responsive particles or complexes are used for isolating substances of interest from non-magnetic test media. The invention relates specifically to a magnetic particle or complex separation assembly having a magnetic support member and a removable invertible rack which can accommodate a variety of specimen containers.

Briefly, in one aspect according to the present invention, the magnetic support member is provided with a base, a vertical member extending therefrom and a handle opposite the base. At least one magnet is embedded within the vertical member. The rack is provided with a pair of spaced apart plates supported by at least one vertical column extending between the plates. The plates each include at least one aperture having different sizes which are adapted to hold specimen containers of desired sizes. The rack further includes a slot extending therethrough dimensioned to receive the vertical member of the magnetic support member. In one position, the rack having at least one specimen container is positioned over the vertical member and rests upon the base of support member. The magnet located within the vertical member of the support member separates the magnetically responsive complexes from the non-magnetic material found within the container. In a second position, the rack is first slidably removed from the support member and inverted so as to accommodate at least one other container having a different size. The specimen rack is positioned onto the magnet support member in similar fashion as mentioned in relation to the first position so that the overall assembly can perform yet another magnetic complex separation. When assembled, the handle extends beyond the specimen rack and, since the specimen rack rests upon the base of the magnetic support member, the entire assembly is easily movable by way of the user grasping the handle.

Advantageously, the apparatus is of relatively simple construction and operation. Most advantageously, it is economical to utilize because it eliminates the need for redundant equipment to accommodate different sized specimen holders. Furthermore, because of its simple design and material selection, it is advantageously easy to clean.

Other features and advantages of the invention will become apparent to those skilled in the art upon review of the following detailed description, claims and drawings in which like numerals are used to designate like features.

BRIEF DESCRIPTION OF THE DRAWINGS

FIG. 9 is an isometric view of the magnetic particle separation assembly according to the present invention with the removable specimen rack inverted and containing a sample of specimen holders illustrating the separation of magnetically responsive complexes from non-magnetic test media.

Before the embodiments of the invention are explained in detail, it is to be understood that the invention is not limited in its application to the details of construction and the arrangements of components set forth in the following description or illustrated in the drawings. The invention is capable of other embodiments and of being practiced or of being carried out in various ways. Also, it is to be understood that the phraseology and terminology used herein is for the purpose of description and should not be regarded as limiting.

DETAILED DESCRIPTION OF THE PREFERRED EMBODIMENTS

Figure 1:
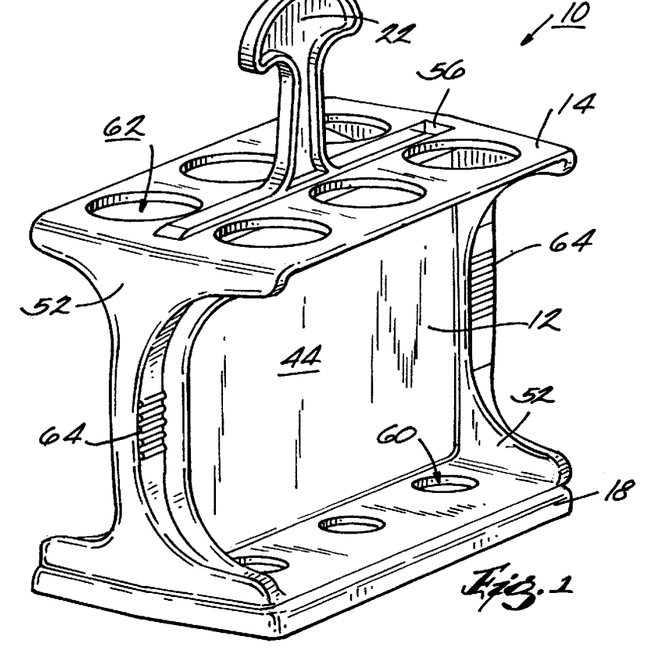
FIG. 1 is an isometric view of a magnetic particle or complex separation assembly illustrating a magnetic support member and a removable invertible specimen rack according to the present invention.
Figure 2:
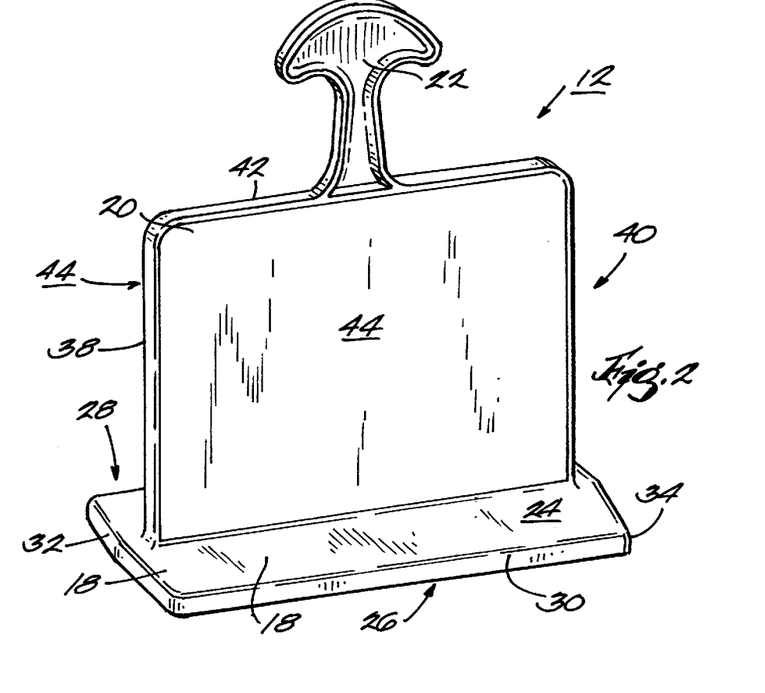
FIG. 2 is an isometric view of the magnetic support member of FIG. 1.
Figure 3:
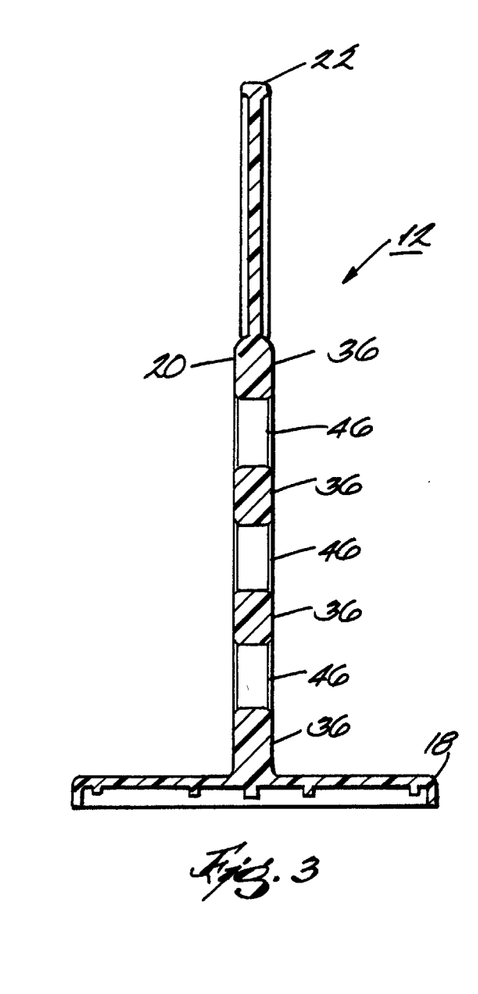
FIG. 3 is a cross-sectional side view of the magnetic support member of FIG. 2 taken along lines 3—3 of FIG. 4 illustrating a plurality of magnets embedded in the magnetic support member.
Figure 4:
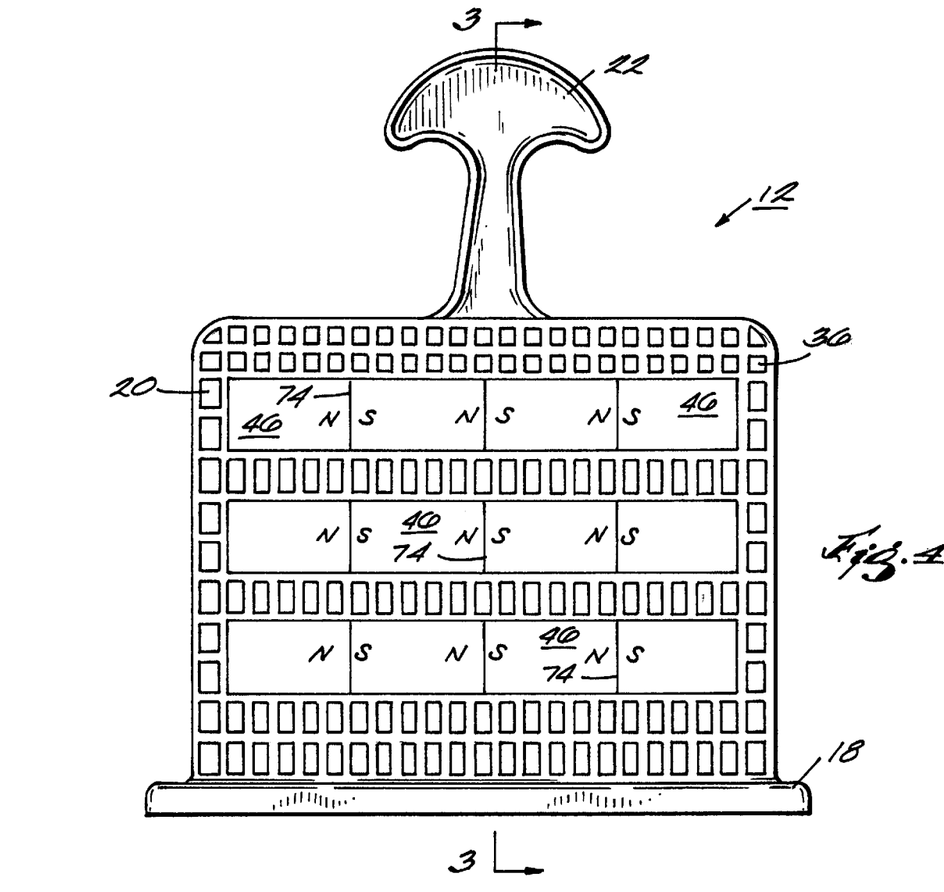
FIG. 4 is a front view of the magnetic support member of FIG. 2 with a front sheet removed further illustrating the plurality of magnets embedded in the magnetic support member.
Figure 5:
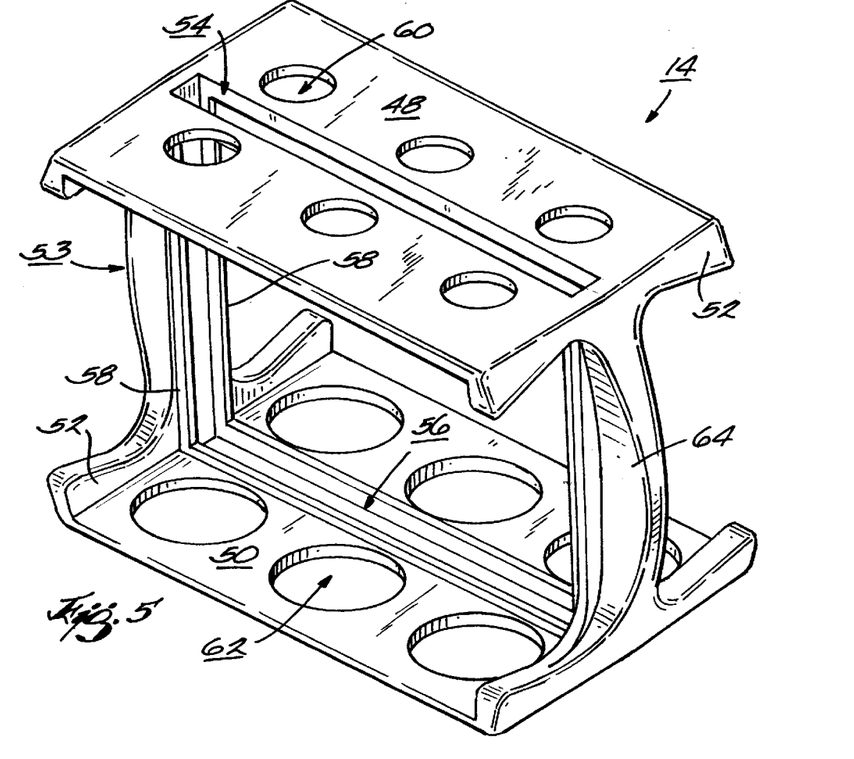
FIG. 5 is an isometric view of the removable invertible specimen rack of FIG. 1.
Figure 6:
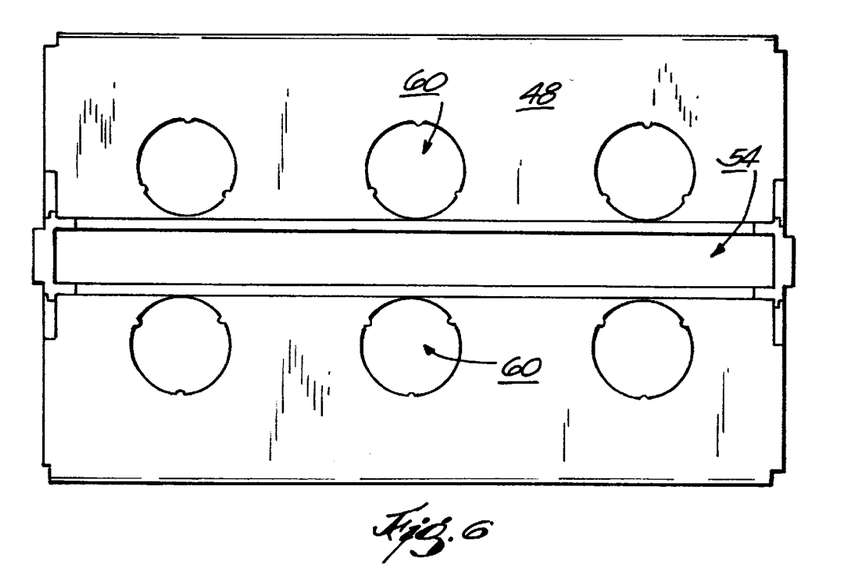
FIG. 6 is a top view of a portion of the removable invertible specimen rack of FIG. 5.
Figure 7:
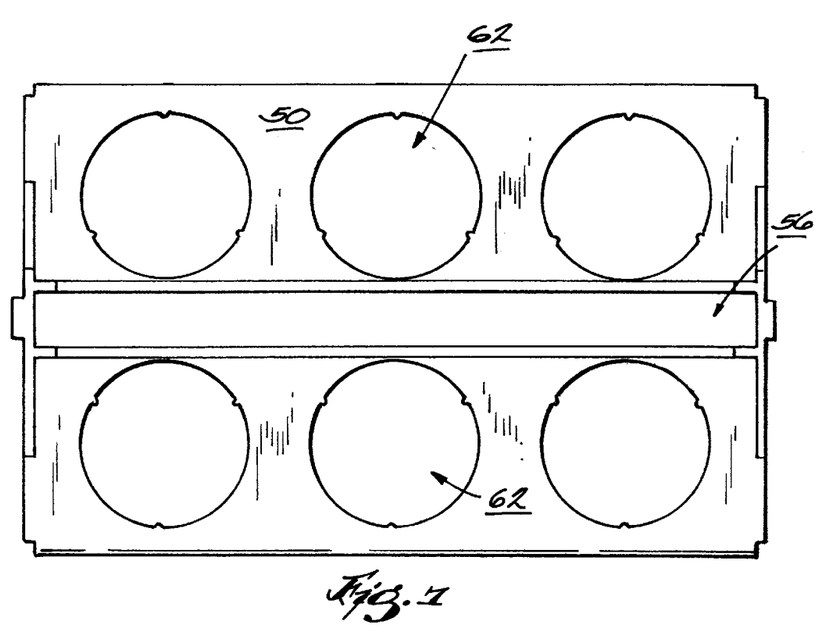
FIG. 7 is a bottom view of a portion of the removable invertible specimen rack of FIG. 5.
Figure 8:
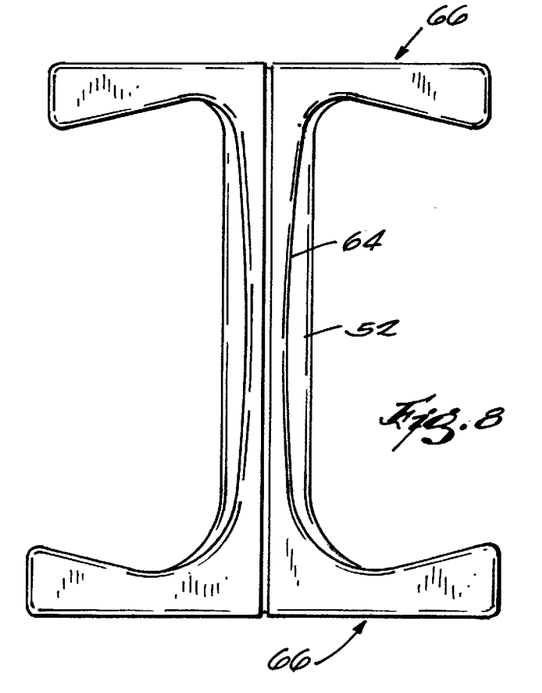
FIG. 8 is a side view of the removable invertible specimen rack of FIG. 5.

FIGS. 1 and 9 depict a preferred embodiment of a magnetic complex separation assembly 10 according to the present invention. FIGS. 2–4 further illustrate a magnet support member 12 shown in FIGS. 1 and 9 according to the present invention. FIGS. 5–8 further illustrate a removable invertible specimen rack 14 also shown in FIGS. 1 and 9 according to the present invention. FIG. 1 shows the assembly 10 without any specimen containers. FIG. 9 shows the assembly 10 with the specimen rack 14 inverted from the orientation shown in FIG. 1 and holding a sample of a plurality of specimen containers 16. FIGS. 2–4 show only the magnetic support member 12 of the assembly 10, the specimen rack 14 having been removed. FIGS. 5–8 show only the specimen rack 14 of the assembly 10, the magnetic support member 12 having been removed.

With reference to FIGS. 1–4, the magnetic support member 12 has a generally inverted "T" shape when viewed from the side (FIG. 3). The magnetic support member 12 includes a generally flat base 18, a vertical planar member 20, and a handle 22. The base 18 is preferably rectangular in shape and includes a top portion 24, bottom portion 26, and sides 28, 30, 32 and 34. The vertical member 20 is supported by base 18 and is preferably centered between sides 28 and 30 extending lengthwise between sides 32 and 34. The vertical member 20 includes a body 36 having cavities therein, sides 38 and 40, a top portion 42, and a pair of outer sheets 44. The handle 22 extends upward from the top portion 42 of vertical member 20. Preferably, the handle 22 is a curved "T" shaped handle as shown.

Preferably, the base 18 is made of an elastomeric material, or a polyvinyl material, or a plastic material, or a polycarbonate material or any durable material capable of resisting periodic contact with water, ethanol, isopropyl alcohol, guanidine, hydrochloric acid, acetone and other common laboratory detergents, and is also capable of withstanding temperatures from about 4 degrees Celsius to about 130 degrees Celsius. Thermosetting and thermoplastic polymeric materials having the performance characteristics described are within the contemplation of the present invention. Although not shown, a rubber pad or the like is preferably attached to the bottom 26 of the base 18 in order to inhibit the assembly 10 from sliding or inadvertently moving when placed on a resting surface such as a countertop.

The body 36 of the vertical member 20 is preferably an injected molded magnetically permeable plastic material, but may be of any material appropriate for use according to the present invention. Even more preferably, the body 36 is of a waffle like structure providing for enhanced strength characteristics the purpose of which can be appreciated by those skilled in the art.

The outer sheets 44 are also preferably made of a magnetically permeable material such as, but not limited to, a polycarbonate material. The outer sheets 44 represent the boundary between the magnets 46 (FIGS. 3 and 4) and the specimen containers 16 (FIG. 9). In order to enhance the separation process, it is desirable to control the distance between the specimen containers 16 and the magnetic field generated by the magnets 46. Therefore, in order to more accurately control the thickness of the sheets 44, the sheets 44 are preferably punched out of a single flat sheet of polycarbonate material. A magnetically permeable material allows magnetic flux lines generated by a magnet to penetrate the material and emanate efficiently therefrom. As with the base material, the body and the sheet material should be compatible with the various chemical agents or solutions commonly used with the various assay techniques in accordance with the present invention.

The base 18, the body 36 of the vertical member 20 and the handle 22 can be individual pieces assembled together according to known methods or the noted components can be of a single construction such as a single injected molded polycarbonate structure according to the various features set forth above.

As best shown in FIGS. 3 and 4, a plurality of magnets 46 are embedded in the cavities of the body 36 of vertical member 20. The magnets 46 are preferably disposed in a horizontal orientation parallel to the base 18 and spaced from the base 18. Preferably, no magnets are located in the base 18 itself. However, it is envisioned that magnets could be properly positioned within base 18 to repel the magnetized material away from the base 18 up and into the magnetic fields generated by the magnets 46. Preferably, the magnets 46 are disposed in three evenly spaced horizontal rows in body 36 with four magnets 46 in each row. The magnets 46 are arranged in the rows such that the north pole "N" of one magnet is adjacent to the south pole "S" of the next positioned magnet, each row being commonly arranged. Pole orientation is generally through the horizontal axis. The significance of the number of magnets 46 and their respective location in the body 36 will be further explained below. The magnets are securely fixed within the rows of the body 36 by applying an adhesive material, such as an epoxy adhesive, to the sides of the magnets. The adhesive makes contact with portions of the body 36 and sets the magnets 46 in place. Prior to installing the magnets 46 into the magnetic support member 12, the back outer sheet 44 may be attached to the body 36 with an adhesive such as an epoxy glue. Once the magnets 46 are set in place, the front outer sheet 44 may be attached to the body 36. Alternatively, both of the sheets 44 may be attached to the body 36 after the magnets 46 are placed within the body 36. The magnets 46 employed generally possess a strong magnetic field. In general, the stronger the magnetic field, the more effective the separation between the magnetically responsive particles or complexes and the non-magnetic material and the faster such separation occurs. The magnets 46 preferably have a magnetic strength of about 36 MegaGuass Oersted (MGO). The magnets 46 are preferably rare earth magnets. More preferably, the magnets are Neodymium/Iron/Boron magnets commercially available from numerous sources known to those in the art.

With reference to FIGS. 5–8, the specimen rack 14 includes a top plate 48, a bottom plate 50, and a pair of opposing vertical members 52 extending between the top 48 and bottom 50 plates. The plates 48 and 50 and vertical members 52 are arranged such that a large open area 53 exists between the top 48 and bottom 50 plates and vertical members 52. The top 48 and bottom 50 plates respectively include slots 54 and 56 (see also FIGS. 6 and 7). The slots 54 and 56 are dimensioned such that the specimen rack 14 is positionable over and onto the magnetic support member 12 as shown in FIGS. 1 and 9. Moreover, the top 48 and bottom 50 plates and vertical members 52 are also dimensioned so that handle 22 extends beyond the top plate 48 of the specimen rack 14 as also shown in FIGS. 1 and 9. Two frame borders 58 extend around the top plate 48, the vertical members 52 and the bottom plate 50 in order to assist in positioning and supporting the specimen rack 14 with respect to the magnetic support member 12. There is no frictional or restrictive fit between the magnetic support member 12 and the specimen rack 14 which would prevent the specimen rack 14 from being freely removed from or positioned onto the magnetic support member 12.

The top plate 48 and bottom plate 50 include a plurality of container holding apertures 60 and 62 (see also FIGS. 6 and 7), the purpose and function of which will be further described below. As shown, the apertures 60 in plate 48 are smaller in dimension than apertures 62 in plate 50, the reason for which will be made clear below. In a preferred embodiment, there are three apertures 60 placed on one side of slot 54 and three apertures 60 placed on the other side of slot 54, and there are three apertures 62 placed on one side of slot 56 and three apertures 62 placed on the other side of slot 56.

The vertical members 52 are generally "I" shaped (FIG. 8) and integral with the top 48 and the bottom 50 plates. As shown, one member 52 is spaced from and substantially parallel to the other member 52. Each member 52 includes a generally centrally located gripper portion 64 which extends outwardly from vertical members 52 and between the top 48 and the bottom 50 plates. The gripping portions 64 are suitably dimensioned to allow a user to easily raise and lower the specimen rack 14 over the magnetic support member 12. Preferably, each of the gripping portions 64 is smooth and curved to prevent injury to the user.

As shown, plates 48 and 50 are generally flat plates designed to independently rest upon the generally flat base 18 of the magnetic support member 12 thereby providing stability to the overall assembly 10. However, it is envisioned that the generally flat edges 66 (FIG. 8) of the vertical members 52 could extend beyond the plates 48 and 50 such that the appropriate edges 66 rest upon the generally flat base 18 of the magnetic support member 12 to provide the desired stability. Generally, the specimen rack 14 is capable of standing on its own apart from the magnetic support member 12 for decanting or pipetting processes, or for other processes associated with the present invention processes.

Preferably, the removable invertible specimen rack 14 is made of a plastic material such as an injected molded polycarbonate material which is resistant to periodic contact with water, ethanol, isopropyl alcohol, guanidine hydrochloride, acetone and common chemical detergents, which is also of sufficient durability to withstand normal handling abuse and mishaps, and which is also capable of withstanding temperatures of about 4 degrees Celsius to about 130 degrees Celsius. The rack 14 has no sharp edges and is safe for a user to handle. Preferably, the rack 14 is attractive being colored in DAY-GLO™ or neon colors for ease of visibility on a lab bench. The rack 14 also can be written on with conventional marking pens, such as SHARPIE™ magic markers. The specimen container apertures of the rack 14 are preferably labeled with numbers or letters to identify each individual tube held by the rack 14.

The specimen rack 14 may be of a single construction such as an injected molded piece of polycarbonate material or the rack 14 may be of a plurality of pieces bound together to create the overall rack assembly 14 as shown. It is envisioned that the specimen rack 14 may consist of two substantially identical components or halves split down the middle of slots 54 and 56. The vertical members 52 may include one or more male/female components such that the two halves fit together. The male/female connectors may be snap-fit connectors, press fit connectors or any number of known connector combinations. An adhesive such as an epoxy may also be used to secure the components or halves together. To further secure the components together such that the halves are not capable of separating from each other unless forced apart or broken, the halves may be welded together in any number of ways known to those skilled in the art depending on the type of material used to make up the halves of the rack 14.

The specimen rack 14 of the assembly 10 is advantageously invertible having different sized receiving apertures 60 and 62 for holding containers 16 of different sizes. Although the top plate 48 and the bottom plate 50 are shown as having six substantially identically shaped respective apertures 60 and 62, the rack 14 may be configured to accommodate any number of different shaped containers depending on the particular application. The preferred arrangement allows the user to observe every sample held by the rack 14. Typically, in prior devices having multi-column, multi-row arrays, some samples are hidden from the user thereby preventing the user to observe the various operations such as the separation operations being performed in each specimen container.

With reference to FIG. 9, sample containers 16 are shown. Each container 16 should have an open top closed by a cap 68 and be preferably tubular in shape. The magnetic particle separation assembly 10 is used to separate or isolate magnetically responsive particles 70 from a non-magnetic test media 72. The removable invertible rack 14 is slidably positioned upon the magnetic support member 12 such that the plate 48 or 50 having the desired sized apertures is positioned above and away from the base 18 closer to the handle 22. An appropriately sized container is chosen so as to be properly positionable in the selected aperture. The container 16 suitably contains a specimen, such as a biological specimen, to be assayed. As is generally understood in the assay art, the specimen is suspended in a non-magnetic test media 72 found in the container 16 or, alternatively, the non-magnetic test media 72 is added to the specimen in the container 16. A magnetically responsive material is added to the container 16 to form magnetically responsive complexes 70. The magnetically responsive complexes 70 are attracted to the magnets 46 found within the magnetic support member 12 and adhere to the sidewalls of the containers 16 as shown in FIG. 9.

In a preferred embodiment, in order to optimize the separation rate, it is desirable to properly manipulate the location of the specimen containers or tubes with respect to the appropriate magnetic field. With reference to FIGS. 4 and 9, the apertures 60 and 62 in the plates 48 and 50 of the specimen rack 14 are arranged such that the containers 16 positioned through the apertures 60 or 62 are centered over north-south pole dividing lines 74 found between adjacent magnets 46. Thus, the front container 16 in FIG. 9 held by aperture 60 in plate 48 is centered over the north-south pole line 74 located furthest to the left as shown in FIG. 4. Since the largest magnetic field is generated nearest the north-south pole line between two magnets, this arrangement will provide a substantially even magnetic field around the container 16 to enhance the magnetic separation and therefore reduce the separation time between the magnetically responsive complexes 70 and the non-magnetic material 72. The preferred arrangement will pull the magnetically responsive material higher and faster in the specimen containers as compared to prior separation devices.

Once assembly 10 is completed, assembly 10 and any containers 16 including any contents therein may be conveniently carried by a user grasping the handle 22. Because the specimen rack 14 rests on the base 18 of the support member 12, the entire assembly 10 is easily movable. The non-magnetic test media 72 may be removed from the container by conventional decanting or aspirating techniques. The caps 68 on the containers 16 will prevent undesired cross contamination of the contents within the containers 16. As should be appreciated, the specimen rack 14 is removed from the magnetic support member 12 by the user grasping the gripper portions 64 of the rack 14 and lifting the rack 14 upwards and away from the support member 12. The containers 16 holding the magnetically responsive complexes 70 may undergo further processing so that the magnetically responsive complexes are freed according to known assay techniques. The assembly 10 is easily cleanable and conveniently usable. The assembly 10 may be cleaned, and/or chemically sterilized between uses according to methods well known in the art. Finally, it should be noted that the support member 12 does not need to be attached to the rack 14 by means of a clip, bead, detect, etc., as is commonly found in prior known devices.

The foregoing description of the present invention has been presented for purposes of illustration and description. Furthermore, the description is not intended to limit the invention in the form disclosed herein. Consequently, variations and modifications commensurate with the above teachings in skill or knowledge of the relevant art, are within the scope of the present invention. The embodiments described herein are further intended to explain the best modes known for practicing the invention and to enable others skilled in the art to utilize the invention as such, or other embodiments and with various modifications required by the particular applications or uses of the present invention. It is intended that the appended claims are to be construed to include alternative embodiments to the extent permitted by the prior art.

Various features of the invention are set forth in the following claims.

What is claimed is:

1. A magnetic separation assembly comprising:
   an invertible rack for holding containers of varying sizes having a magnetically responsive complex suspended in a non-magnetic media therein; and
   a magnetic support member adapted to receive said invertible rack such that the magnetically responsive complex is separated from the non-magnetic material when said rack is positioned on said support member, wherein when said rack is positioned on said support member in a first position, at least one container of a first size is held by said rack, and wherein when said rack is positioned on said support member in a second, inverted position, at least one other container of a second size is held by said rack.

2. A magnetic separation assembly according to claim 1, wherein said invertible rack includes a pair of spaced apart opposing plates separated and supported by at least one vertical member, wherein each plate contains at least one different sized aperture adapted to hold individual containers.

3. A magnetic separation assembly according to claim 1, wherein said invertible rack includes at least one slot located therethrough and dimensioned to receive a portion of said magnetic support member so that said invertible rack is slidably positioned on or removed from said magnetic support member.

4. A magnetic separation assembly according to claim 3, wherein said invertible rack includes at least one frame border positioned around said slot so as to further guide and support said rack with respect to said support member.

5. A magnetic separation assembly according to claim 1, wherein said invertible rack is made of a polycarbonate material.

6. A magnetic separation assembly according to claim 1, wherein said magnetic support member includes a base and a vertical member extending therefrom which has a plurality of magnets embedded therein for separating the magnetically responsive complex from the non-magnetic material.

7. A magnetic separation assembly according to claim 6, wherein each container having magnetically responsive particles to be separated from the non-magnetic material is centered over a respective north-south pole dividing line located between adjacent magnets.

8. A magnetic separation assembly according to claim 7, wherein said rack includes at least three apertures adapted to hold individual containers and, wherein said magnets are disposed in at least three horizontal rows with at least four magnets located in each row.

9. A magnetic support assembly according to claim 6, wherein said vertical member is made of magnetically permeable material.

10. A magnetic support assembly according to claim 1, wherein said magnetic support member further includes a handle such that the overall assembly is easily movable.

11. A magnetic separation assembly comprising:

a removable, invertible specimen rack having an upper plate and a spaced apart lower plate, each plate having at least one aperture of different sizes located therethrough and a slot extending vertically therethrough, said rack further including at least one vertical member extending between said plates and connecting said plates together; and a magnetic support member having a base and a vertical member extending therefrom and having a plurality of magnets embedded therein such that said vertical member of said support member fits in said slot of said rack so that, in one position, said rack is positioned on said support member whereby at least one container having magnetically responsive particles in a non-magnetic media is held by said at least one aperture in said rack adjacent to said magnet support member thereby allowing the magnetically responsive complex to be separated from the non-magnetic media and, in a second inverted position, said rack is positioned on said support member whereby at least one other container of a different size having magnetically responsive complex in a non-magnetic media is held by said at least one other aperture in said rack adjacent to said magnetic support member thereby allowing the magnetically responsive complex to be separated from the non-magnetic media.

12. A magnetic separation assembly according to claim 11, wherein said invertible rack includes at least one frame border positioned around said slot so as to further guide and support said rack with respect to said support member.

13. A magnetic separation assembly according to claim 11, wherein said invertible rack is made of a polycarbonate material.

14. A magnetic separation assembly according to claim 11, wherein each container having the magnetically responsive complex to be separated from the non-magnetic material is centered over a respective north-south pole dividing line located between adjacent magnets.

15. A magnetic separation assembly according to claim 14, wherein said rack includes at least three apertures adapted to hold individual containers and, wherein said magnets are disposed in at least three horizontal rows with at least four magnets in each row.

16. A magnetic support assembly according to claim 11, wherein said vertical member is made of magnetically permeable material.

17. A magnetic support assembly according to claim 11, wherein said magnetic support member further includes a handle such that said overall assembly is easily movable.

18. A magnetic support assembly according to claim 11, wherein said rack further includes at least one gripper portion located on said vertical member so that said rack is easily slid onto or removed from said support member.

19. A method of separating a magnetically responsive complex from a non-magnetic test media using a magnetic particle separation assembly comprising the steps of:

selecting a magnetic separation assembly comprising an invertible rack for holding specimen containers of varying sizes and a magnetic support member adapted to receive said invertible rack, said rack being positionable on said support member in at least a first position and a second, inverted position, such that when said rack is positioned on said support member in said first position, at least one container of a first size is held by said rack, and such that when said rack is positioned on said support member in said second, inverted position, at least one other container of a second size is held by said rack;

inserting at least one container holding a specimen to be assayed suspended in a non-magnetic test media into said invertible rack;

adding magnetically responsive material to the container and forming a magnetically responsive complex;

positioning said rack onto said magnetic support member by sliding said rack over a portion of said magnetic support member; and allowing the magnetically responsive complex to be attracted by a magnetic field emanating from said magnetic support member thereby separating the magnetically responsive complex from the non-magnetic test media.

20. The method of claim 19, further comprising the step of removing the non-magnetic test media from the container or containers.

21. The method of claim 20, further comprising the step of removing said rack from said magnetic support member by lifting said rack away from said support member.

22. The method of claim 21, further comprising the step of inverting said rack and inserting at least one other container of a different size into said rack and repeating the remaining steps.

* * * * *